(12) United States Patent
Oshida (10) Patent No.: US 6,312,473 B1
(45) Date of Patent: Nov. 6, 2001

(54) ORTHOPEDIC IMPLANT SYSTEM

(76) Inventor: Yoshiki Oshida, 310 Haddonfield Dr., DeWitt, NY (US) 13214

( * ) Notice: Subject to any disclaimer, the term of this patent is extended or adjusted under 35 U.S.C. 154(b) by 0 days.

(21) Appl. No.: 09/421,390

(22) Filed: Oct. 20, 1999

Related U.S. Application Data (63) Continuation of application No. 08/678,676, filed on Jul. 11, 1996, now Pat. No. 6,066,176.

(51) Int. Cl.⁷ ........................................... A61F 2/34
(52) U.S. Cl. .................. 623/23.55; 623/23.3; 623/22.33; 623/22.39
(58) Field of Search ............................ 623/11.11, 16.11, 623/23.15, 23.26, 23.29, 23.3, 23.36, 23.37, 23.58, 23.59, 23.6, 23.61, 23.62, 23.63, 23.55, 23.53, 22.53, 22.39

(56) References Cited

U.S. PATENT DOCUMENTS

| | | | |
|---|---|---|---|
| 4,500,658 | * 2/1985 | Fox ...................................... | 523/117 |
| 4,714,721 | * 12/1987 | Franek et al. ......................... | 523/113 |
| 4,735,625 | * 4/1988 | Davidson .............................. | 623/16 |
| 5,035,713 | * 7/1991 | Friis ..................................... | 623/23.52 |
| 5,171,288 | * 12/1992 | Mikhail et al. ....................... | 623/23 |

* cited by examiner

*Primary Examiner*—David J. Isabella
(74) *Attorney, Agent, or Firm*—Breiner & Breiner, L.L.C.

(57) ABSTRACT

It is an object of the present invention to provide an improved orthopedic implant system with satisfied biological, mechanical and morphological compatibilities.

Solid metal femoral stem and solid metal acetabular head are covered with diffusion-bonded foamed-shaped sheet made of commercially pure titanium or titanium alloy(s). The open-cells in said foamed metal sheet are impregnated with biocompatible polymethyl methacrylate resin cement, which is reinforced with selected oxides including alumina, magnesia, zirconia, or a combination of these oxides along with an application of a small amount of a metal primer agent.

6 Claims, 5 Drawing Sheets

ORTHOPEDIC IMPLANT SYSTEM

This is a continuation of application Ser. No. 08/678,676 filed Jul. 11, 1996, now U.S. Pat. No. 6,066,176.

TECHNICAL FIELD

The present invention relates to an orthopedic implant system. More specifically, the present invention relates directly to a surface modification of the total hip prothesis system to improve the bony ingrowth for a better biological fixation, and to modify the bone cement in terms of both mechanical and physical properties.

BACKGROUND

Total hip replacement prostheses have now been in use clinically for over 35 years. Most experience has been gained in the hip joint, where naturally, the prothesis is of the ball-head of the femoral stem and socket-type cup of the acetabular component. More recently reconstruction of the knee, elbow, shoulder and ankle have been attempted using prostheses of more varied mechanisms and design, although the basic concept for designing these prostheses remains unchanged.

One of the many universal requirements of implants, wherever they are used in the body, is the ability to form a suitably stable mechanical unit with the neighboring tissues. A loose (or unstable) implant may function less efficiently or cease functioning completely or it may induce an excessive tissue response. In either case it may cause t he patient discomfort and pain and in several situations a loose implant is deemed to have failed and has to be surgically removed. Total hip replacement prostheses have focused attention onto this stability question of the propensity for the load-transmitting prostheses to become over a period of time.

There are several ways in which the stability problem could be approached. One could consider a chemical approach in which adhesives were used to bond prostheses to tissues. Secondly, there is the mechanical approach and at least three different methods have been tried. One is now in routine clinical use and involves the interposition of a mass of acrylic "cement" into the space between prothesis and bone. There is no adhesive action as such, but rather a grouting effect which gives a mechanically stable unit and provides uniform load transfer.

Alternatively, one may choose an exceptionally inert material and prepare an accurate, well designed bed in the bone for the prothesis. The initial stability and the minimization of differentiation processes around the prothesis may allow new bone to grow right up to the prothesis surface to give a long-term stability. Using high density alumina ceramic appears to be a very bio-inert material and is a suitable candidate for these prostheses. However, as one might expect, the situation is not quite this simple and loosening can occur, even with very accurate bone-bed preparation. Surface macro-profiles on the prothesis may improve the stability but even here the limitations of this primary mechanical interlocking are shown.

In a third mechanical approach, the tissues do the work rather than the prothesis or a cement for this relies on tissue ingrowth into a micro-porous structure.

The important point is the extent of the fibrous tissue layer, if any, that forms between the material and the bone. It can be explained that it may need a biodegradable cement or temporary fixation to give initial stability while the necessary bone remodelling takes place to achieve a fibrous-tissue-free interface.

The development of porous implant was based on three key needs; biocompatibility through the use of ingredients (polytetrafluoroethylene and carbon fibers) that are stable in the body milieu and induce minimal biological disturbance through surface effects; biofunctionality through the selection of a modulus close to that of soft tissue and spongy bone (4 MPa); and maximum porosity (80 per cent void, 100~500 $\mu$m diameter) and inter-pore connections (100~200 $\mu$m) for tissue ingrowth consistent with appropriate bulk mechanical properties (ultimate tensile strength 1 MPa).

Figure 1:
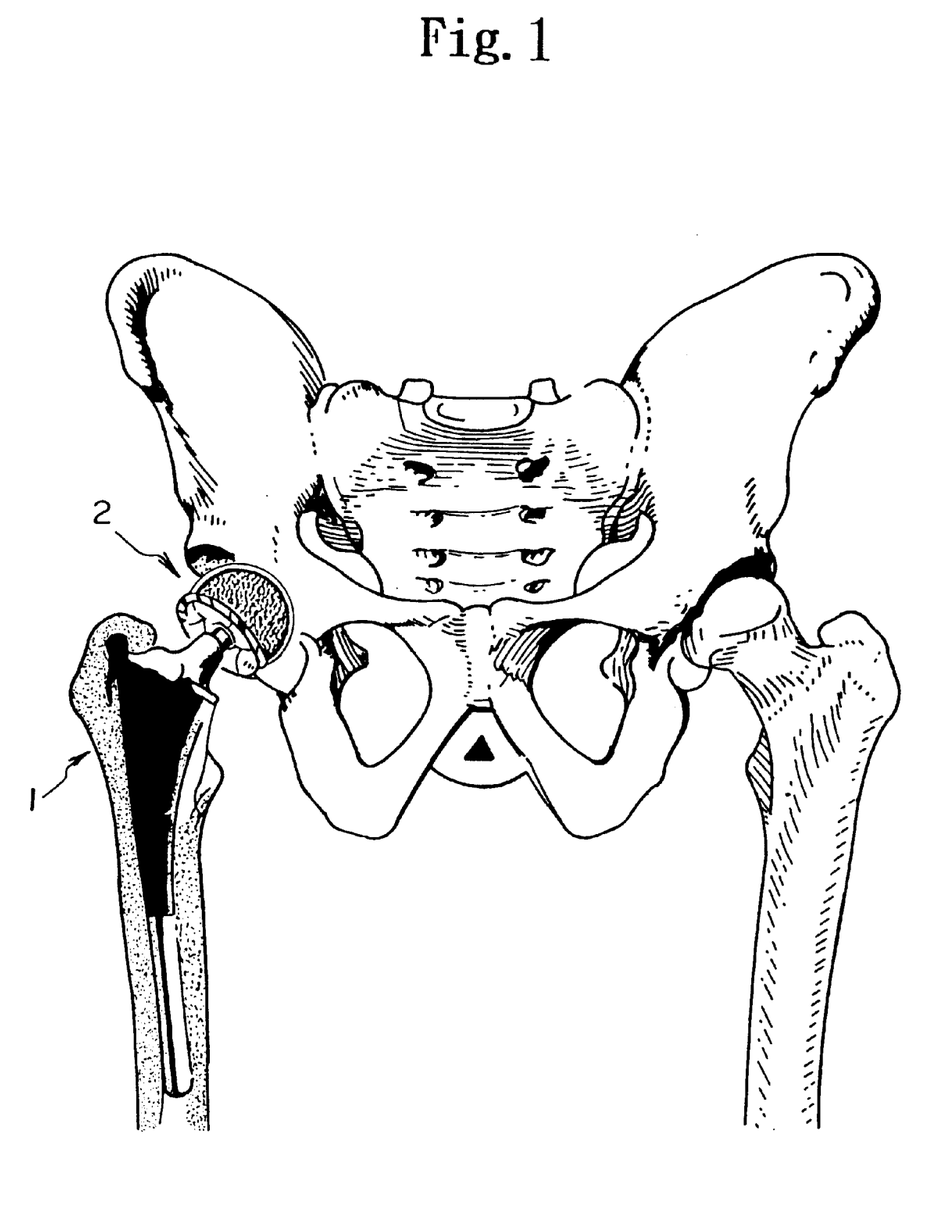
FIG. 1 shows a general view to show how the stem with a ball head prosthesis 1 is implanted into a femur and how the socket-type cup 2 with insert potion is implanted into an acetabulum.
Figure 2:
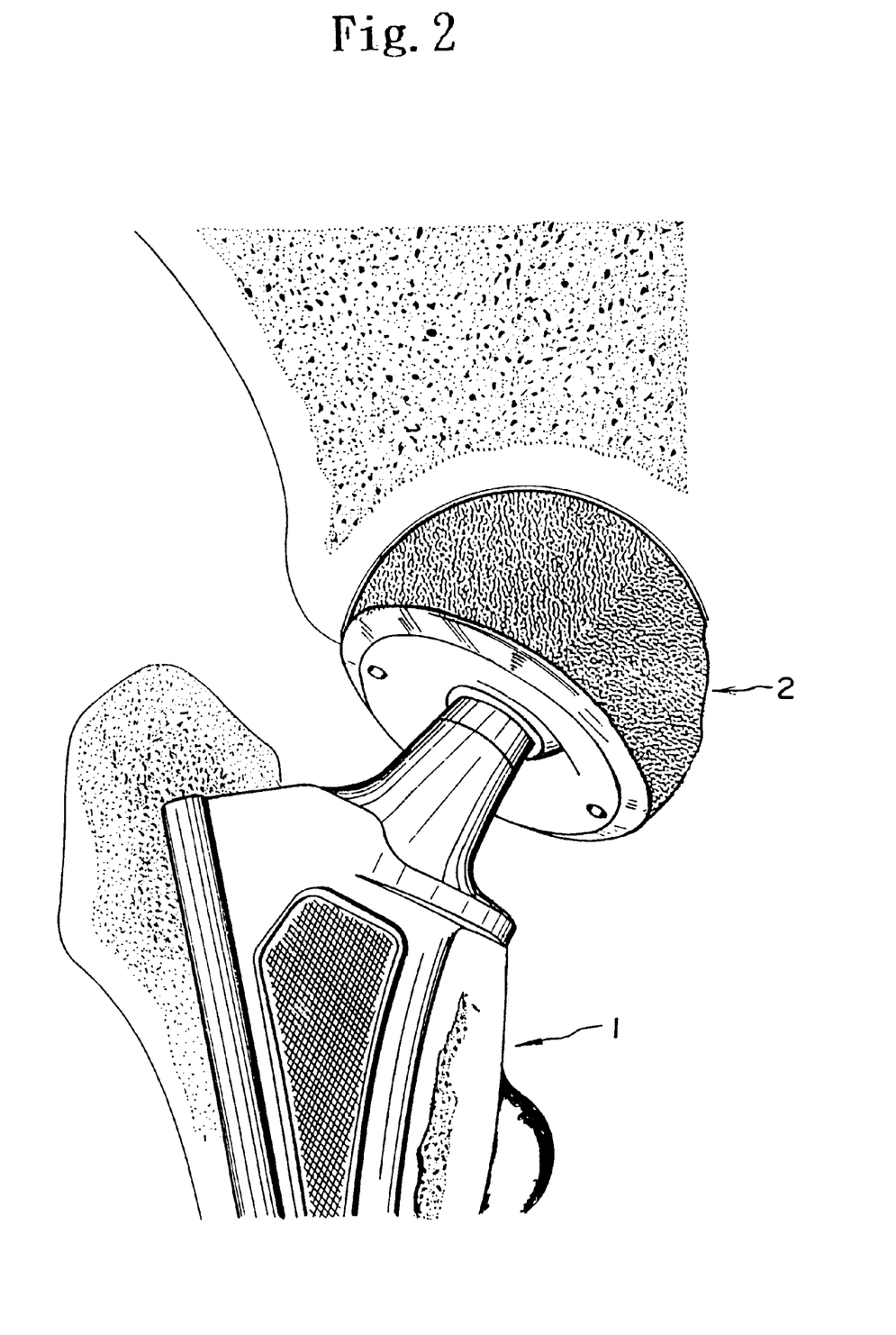
FIG. 2 shows an enlarged view showing a jointing manner of said ball head portion of the femoral prosthesis 1 into an inner insert portion of the acetabular cup 2.
Figure 3:
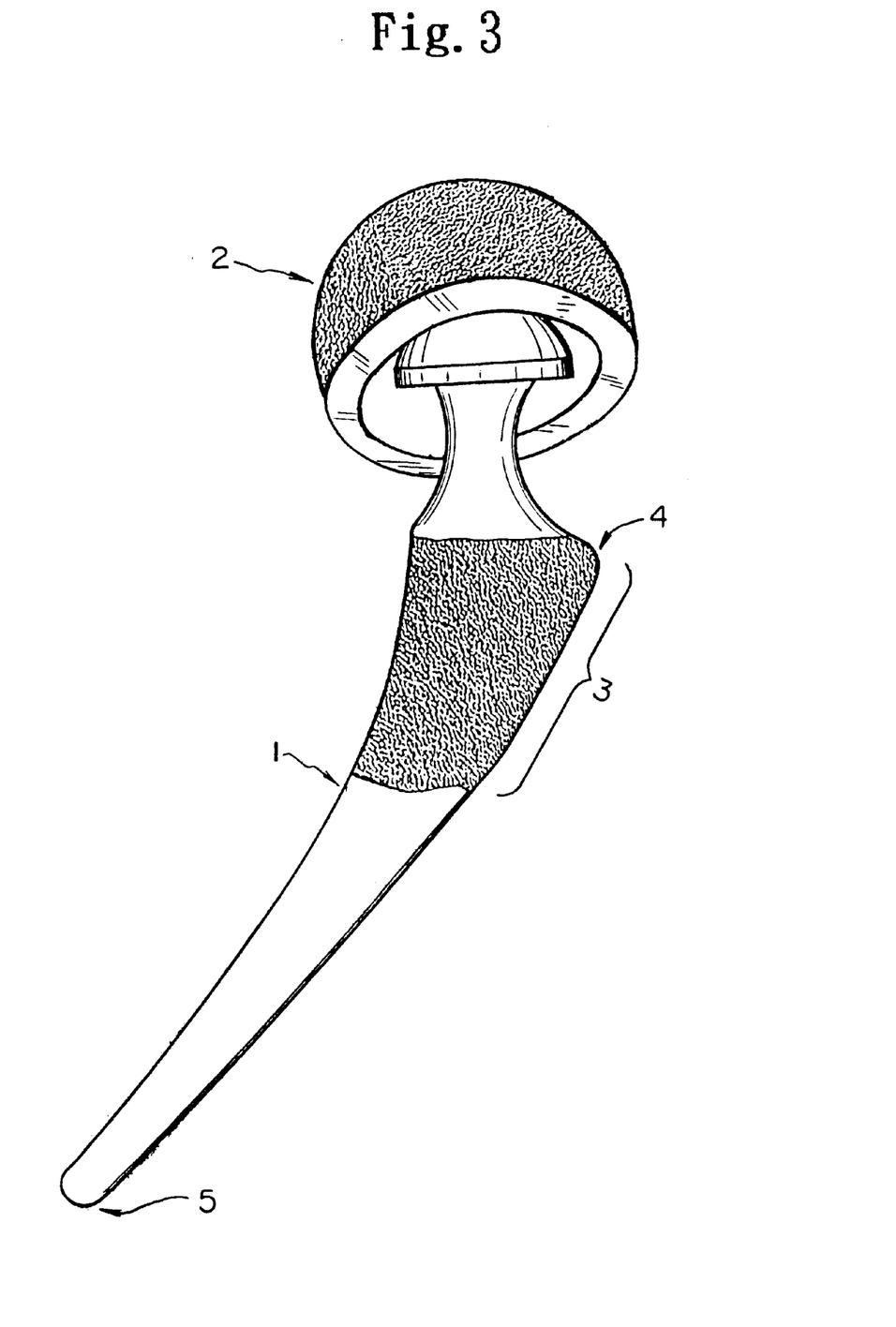
FIG. 3 shows a complete view of an orthopedic implant system, wherein there is a femoral prosthesis 1, an acetabular cup 2, a stem proximal portion 3, a collar portion 4, and a distal portion 5.

Referring to FIGS. 1 and 2, typical type of an orthopedic implant, particularly the total hip prothesis system, consists of a femoral prothesis 1 which has a long stem extending from a proximal portion with a ball-head portion to a distal portion and is inserted into a femur, and an acetabular socket-type cup 2 with an interlocking ring and insert which is implanted into an acetabulum. FIG. 3 shows an example of the total hip prothesis stem in which said femoral prothesis stem is interlocked into an acetabular cup (not shown).

It has been, for a long time, recognized that any type of implants (whether it is a dental implant or an orthopedic implant), should possess a biological compatibility against an implant-receiving surrounding hard and soft tissues. Accordingly, the materials for implants are limited to a certain type of materials, including a commercially pure titanium (CPT), T-6Al-4V alloy, Co—Cr or Co—Cr—Mo alloy, Fe—Cr—Mn—Ni—Mo—Nb—Si alloy, AISI Type 316L stainless steel, and some ceramic materials including pure alumina and the synthetic hydroxyapatite.

Similar type of materials used for the femoral prostheses can be found for the acetabular cups. One exception is that the ultra high molecular weight polyethylene (UHWMPE; average molecular weight is about more than 5,500,000) is a mainly selected material for the acetabular socket-type cup.

For these femoral prostheses and acetabular cups, several surface modifications have been proposed and used for enhancing the mechanical retention and promotion of the bony ingrowth.

In the ORTHOMET® system, very small size of commercially pure (CP) titanium beads are plasma-coated onto Ti-6Al-4V femoral stem to produce a porosity of about 50%. The CPT beads are coated on a proximal portion 3 in FIG. 3.

In the KYOCERA® system, CPT is coated onto a proximal portion of the Ti-6Al-4V stem material by the inert gas shielded arc spray to generate a coarse surface.

In the DePuy® system, very fine size of CPT beads are also coated on a proximal portion of the femoral stem to ensure a complete contact with the relatively weak cancellous bone structure.

In the development history of the bony ingrowth type artificial joint prostheses, there are two major design concepts available; namely, (1) a micro-fit type (or bone ongrowth type) in which grooves are formed on the surface of the implants, and (2) a micro-interlock type (or bone ingrowth type) in which the surface of implants is formed to be porous structure. In MULTILOCK® system, the mesh pad made of titanium fibers is bonded onto the proximal portion of the femoral prothesis through a solid state diffusion bonding technique.

In DePuy® system and STRAYKER® system, Co—Cr beads (approximately 150~300 $\mu$m diameter) are sprayed or sintered to Co—Cr femoral stem material to generate an average pore size of 275 $\mu$m.

In MATRIX HIP® system, the proximal portion of Co—Cr femoral stem was machined to create the macro- and micro-texturing for a reduced interfacial shear stress.

In ORTHOMET® system, polymethyl methacrylate (PMMA) resin studs are bonded as a pre-coating on an entire stem portion to enhance the bonding strength with the bone cement when the femoral stem is implanted into the cement mantle.

Moreover, in KYUCERA® system, synthetic hydroxyapatite is plasma-coated on the proximal portion of the stem to have an average particle size of 50 μm. Alternatively, the proximal portion is subjected to a blasting to form a micro-textured structure.

Moving to the acetabular socket-type cups, in ORTHOMET® system, CPT beads are plasma-coated onto Co—Cr alloy to reduce the occurrence of the loosening.

In a similar manner, in STRYKER® system, CPT beads are bonded on the outer shell of the socket to enhance the mechanical retention.

In MULTILOCK® system, a plurality of PMMA studs are adhered on the outer surface of the acetabular head to promote a chemical bond with PMMA in the cement mantle.

In AcSysHA® system, synthetic hydroxyapatite is coated on an entire outer surface of the acetabular cup.

In the most outer shell of the acetabular head, a plurality of multi-hole, in-hole or cluster-hole are formed to promote the bony ingrowth activity.

Some of the aforementioned surface modification, particularly hydroxyapatite coating, are related to the mechanical comnatibility (which is the second compatibility required for the successful implant system). As discussed previously, the prostheses, particularly surface zone thereof, should respond to the load-transmitting function.

Suppose that an implant made of Ti-6Al-4V alloy is used. It is reported that strength and modulus of elasticity (MOE) of Ti-6Al-4V alloy are in ranges of 900~1200 MPa and 200~300 GPa, respectively. On the other hand, the strength and MOE of an implant-receiving bone has ranges of 100~200 MPa and 9~12 GPa, respectively. There are great differences in mechanical properties between these materials. With respect to the load-transmitting function, the strain field should be continuous. If the strain field in a metallic implant and bone system is not continuous, then the interface is not adhered and is easily debonded. However, even the strain field is continuous, the stress field has always a discontinuity due to the differences in MOE values between two dissimilar materials. If the discontinuous stress at an interface exceeds the interfacial bonding strength, then the bonding is failed.

Based on the above discussion, it is easily understood that the synthetic hydroxyapatite is plasma-coated onto the metallic implant, since the hydroxyapatite has not only an excellent biocompatibility, but it also exhibits the strength (400~800 MPa) and MOE (40~120 GPa) which are just between those values for Ti-6Al-4V and the implant-receiving bone structure. This is what is claimed as the second compatibility; namely, a mechanical compatibility to form a continuous gradient functional (in terms of mechanical property) structure.

Furthermore, the third compatibility should be included to the aforementioned currently accepted compatibilities; that is a morphological compatibility. In a scientific article published by this inventor (entitled "Fractal Dimension Analysis of Mandibular Bones: Toward a Morphological Compatibility of Implants" in Bio-Medical Materials and Engineering, Vol. 4 No. 5, pp.397/407, 1994), surface morphology of successful implants has a limitation of the average roughness (1~500 μm) and average pore size (10~500 μm), regardless of types of implant materials including metallic materials, ceramic materials and polymeric materials. If the pore size is smaller than 10 μm, the surfaces will be more toxic to fibroblastic cells and has an adverse effect on cells due to their physical presence independent of any chemical toxic effects. If the pore size is larger than 500 μm, the surface does not exhibit any sufficient structural integrity.

Moreover, as discussed previously, a mesh pad made of titanium beads is coated on the proximal portion of the femoral stem to promote the bony ingrowth. However, the opening space is not morphologically compatible to surrounding bone, particularly the cancellous bone. Any one of the beads (either made of Ti, hydroxyapatite, or PMMA) does not create sufficient opening space for the bony ingrowth and, then, is not morphologically compatible.

Successful implant system is relied not only on these three compatibilities, but also on cementation of the space gap between the prothesis and the vital bone.

With a certain type of the femoral prothesis, a ring-shaped cement riser made of PMMA is installed at a collar portion of the proximal part 4 in FIG. 3 and at a distal portion thereof 5 in FIG. 3. However, in the most femoral prostheses and acetabular cups, there is no pre-formed cement riser. Hence, during a surgical operation, cement mantle should be fabricated. Normally, the bone cement or bone paste consists of a mixture of PMMA resin and crushed bone autograft.

For a normal practice, the kneaded cement is used under a relative low viscosity. In order to keep the low viscous cement, the cement is cooled to prolong the wetting time until 90 seconds, which is advantageous, but the strength of the cement is slightly reduced. In order to compensate the reduced mechanical strength, the cement is mixed in vacuum to control the porosity.

Even with the aforementioned efforts, there are several important factors unsolved. These include (1) the heat generated during the polymerization of methyl methacrylate monomer, (2) the polymerization shrinkage, and (3) insufficient break strength and the modulus of elasticity.

Regarding the heat generated, the temperature rise is a function of the rate of polymer formation, or curing rate, rather than the rate of polymerization of a single polymer. Furthermore, the temperature rise is dependent of the rate of heat evolution and not necessarily upon the total heat evolved. Depending on the polymer formation rate, the temperature rise is reported in a range of 70 to 120° C., which may irritate the surrounding hard and soft tissue and cause unexpected damage on them.

With regard to the polymerization shrinkage, it is reported that when methyl methacrylate monomer is polymerized, the density changes from 0.94 gm/cm$^3$ to 1.19 gm/cm$^3$. This change in density results in a volumetric shrinkage of 21 per cent, usually called the polymerization shrinkage. However, about one third in weight of the resin is monomer, then the volumetric shrinkage will be about 7% (that is approximately 2% of linear shrinkage). This amount of shrinkage is still too large and causes a dimensional accuracy and stability.

Regarding the mechanical properties, it is reported that the compressive strength of PMMA is about 50~70 MPa; while the bending strength is about 60~65 MPa. The modulus of elasticity in compression is 1.8~2.0 GPa; while MOE value under the bending mode is about 1.3~1.5 GPa. These are lower than those values for bone structure.

OBJECTIVE OF THE INVENTION

It is, therefore, an object of the present invention to provide an orthopedic implant system which meets all three compatibilities (namely, biological, mechanical, and morphological), so that a strong interlocking fixation due to the bony ingrowth can be achieved.

It is another object of the present invention to provide the modified and reinforced polymethyl methacrylate resin as a bone cement as well as a material which can be used as a provisional crowns and bridges in dentistry, having a less temperature rise and shrinkage during the polymerization process.

CLOSURE OF THE INVENTION

Figure 4:
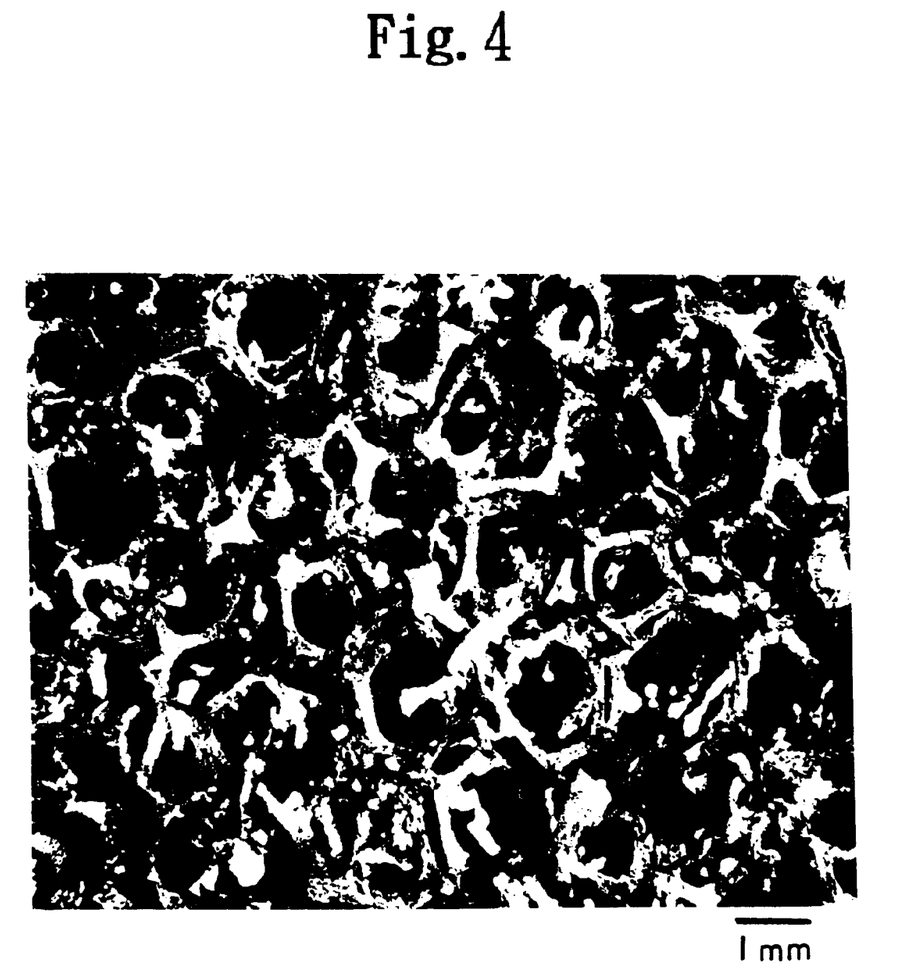
FIG. 4 depicts a microstructure of Al alloy foam network, taken under a magnification of X10.

In order to achieve the first object, it was found that the foam-shaped materials exhibit a continuously connected ligamented, reticulated open-cell geometry having a duo-decahedronal cell shape, as seen in FIG. 4. The foam-shaped material is presently available in a density ranging from 1 to 20% theoretical and a cell density of 10~50 cells per linear inch, with material density and cell density independently variable.

Foamed material is presently produced in a wide range of plastics, metals and composites having either solid or tubular ligaments. The metals include aluminum, nickel, copper, silver, zinc, lead, tin, magnesium, and stainless steel. The example shown in FIG. 4 is a product by ERG, Inc., using Al-alloy (6101-T6). This aluminum foam metal has a modulus of elasticity in tension is 48~83 MPa (for 6~10% nominal density) and an MOE in compression of 69~114 MPa (for 6~10% nominal density).

The patent literature (U.S. Pat. No. 2,434,775 January 1948, and U.S. Pat. No. 2,553,016, May 1951) describes a foam-like metal made of heating under pressure a mixture or composite of a metal and gas-forming material to a temperature above the melting point of the base metal and then releasing the pressure to permit the gas-forming material to decompose. On solidifying, the metal assumes a foamed structure.

Basically, the procedure for producing a foamed aluminum body comprises adding a foaming agent to a pool of molten aluminum or aluminum alloy, mixing thoroughly, and pouring into a mold.

An initial proposal by B. Sosnik in 1948 (U.S. Pat. No. 2,434,775 and U.S. Pat. No. 2,553,016) was concerned with the making of foamed metals with the aid of an alloying constituent to form a vapor phase at metal fusion temperatures. According to Sosnik, this can be achieved by using a metal mixture made up, e.g., of 10% Hg and 90% Al. This is fused in a pressurized chamber, then the pressure is reduced to atmospheric so that Hg-vapor filled cavities may form, which gives rise to a foamed structure when the metal is allowed to cool. The procedure developed by Bjorksten Research Laboratory Inc., Madison Wis., in 1956 is based on a similar idea, i.e., the decomposition of metal hydrides, for example titanium or zirconium hydrides, or of carbonates etc., in melts of metal alloys with a wide solidification range, preferably Al:Mg melts.

To ensure that the process operates under optimum conditions, the gas-separating additive must be perfectly wetted with the base metal. When necessary, this must be achieved by grinding the metal hydride in a preliminary melt of the base metal. If the metal hydride decomposes at temperatures below the fusion temperature of the base metal, grinding has to be performed in pressurized atmosphere. The premix is allowed to solidify and is reduced to power before being added to the bulk quantity of the powdered or granulated base metal. If titanium hydride is used, the amount to be added should be about 10%. If the mixture when ready contains a gas-separating additive which decomposes at temperatures below the fusion temperature of the base metal, it is placed on a conveyor belt of a pressurized installation, passed through a heating zone for melting—while suppressing the decomposition of the additive—and then retransferred into normal atmosphere. The foamed metal which forms instantaneously is then solidified by immediate quenching in water. In this way, foamed aluminum plates can be made in thicknesses of up to 200 mm. Because of the nature of the material, these plates will not solidify with a uniform density, the gas bubbles ranging from <1 mm in diameter at the surface to about 6 mm in diameter in the core of the plate. The density of the material can be adjusted to values of from 0.2 to 0.5 gm/cm$^3$. Unlike the honeycomb material, the spherical pores provide the foamed metal with isotropical properties in all directions.

Although titanium foamed metal is not available currently, we are furnished with a technology to fabricate titanium foamed metal. According to the aluminum foam metal data as described before, the strength (50~70 MPa) of foam Al alloy is about 30% of strength of solid Al alloy, and MOE values (1.3~2 GPa) of foam Al alloy is about 3% of the solid Al alloy. Hence, it is expected that the strength of CP titanium foam will be about 90 MPa (which is 30% of strength of solid CP titanium) and the MOE of CPT will be 3.06 GPa (which is about 3% of the solid CP titanium). By the same token, 285 MPa will be expected for the strength of foam Ti-6Al-4V alloy and 3.42 GPa will be speculated for the MOE value of the foam Ti-6Al-4V alloy.

Hence, these values of strength and MOE values are close to somewhat between the solid metallic materials (Ti-6Al-4V, CPT or the others) and bone structure as mentioned previously. Hence the biological and mechanical compatibilities will be satisfied by using Ti foam metal at the interface of the prothesis and receiving vital bone structure.

Surprisingly, it is observed that the continuously connected ligamented, reticulated open-cell geometry of the foam metal (as seen in FIG. 4) bears a very resemblance to the cancellous (or spongy) bone. Hence the third morphological compatibility is now satisfied.

The present invention provides a new orthopedic implant system which comprises of a solid stem and head, foamed sheet made of biocompatible materials (mainly CPT or Ti-based alloy) being covered over partial or entire surfaces of said stem and head, and reinforced PMMA resin serving as a bone cement partially being impregnated into open-cells of said foamed metallic sheet. Hence the presently invented implant system has a uniquely divided but structurally continuous three layers; (i) a solid metallic stem or head, (ii) coarse foamed metallic sheet which is impregnated by the reinforced PMMA resin (which will be described later in a great detail), and (iii) a layer of the reinforced PMMA resin.

As described briefly in the above, it is speculated that the foamed CPT or Ti-6Al-4V sheet will possess mechanical properties somewhat between those values of solid COT of Ti-6Al-4V and those values of the vital bone structure. But the estimated strength and MOE values of foamed Ti sheet are not good enough to find themselves exactly between those values; particularly the estimated MOE value (3~3.4 GPa) of foamed Ti metal sheet is lower than the MOE value range (9~12 GPa) for bone.

Hence it is needed to modify the mechanical properties of PMMA resin which is impregnated into open-cells of said foamed sheet. In order to reinforce PMMA (polymethyl methacrylate) resin, it was proposed to mix with a synthetic Formica or plasma-treated woven polyethylene fiber as a reinforcement element as a prior art. These modifications have been proposed only for a purpose when PMMA resin is used for fabricating provisional crowns and bridges. These reinforcing filaments are relatively expensive and alignment of filaments is troublesome and time-consuming. In the present invention, therefore, the dispersive strengthening concept, which is normally employed in the reinforcing the composite materials, is used. For reinforcing dispersive particles, metallic oxides and synthetic hydroxyapatite are used in the present invention.

Moreover, foam metal sheet (of Al alloy) was impregnated with PMMA resin which is reinforced with said metallic oxides. It was found that a certain type of metallic oxides (such as $Al_2O_3$, MgO, $ZrO_2$) improved the mechanical strengths as well as the modulus of elasticity of PMMA matrix, and reduced the temperature rise during the polymerization process and the extent of the polymerization shrinkage. Furthermore, if PMMA is mixed with these metallic oxides and embedded into a metallic foam network, it was found that this modification provided us the best results of all in terms of mechanical properties (strength and MOE values) and physical properties (temperature rise and polymerization shrinkage).

BRIEF DESCRIPTION OF THE DRAWINGS

The above and many other objectives, features and advantages of the present invention will be more fully understood from the ensuing detailed description of the preferred embodiment of the invention, which description should be read in conjunction with the accompanying drawings.

FIG. 5(A) shows the bonding manner of titanium or titanium alloy foam network sheet to the outer peripheral surface of the acetabular cup, according to the present invention.

FIG. 5(B) and (C) show the different ways to bond the titanium or titanium alloy foam network sheet onto the proximal portion (B) or entire surface of the stem portion (C) of the femoral prothesis, according to the present invention.

PREFERRED EMBODIMENTS

Figure 5:
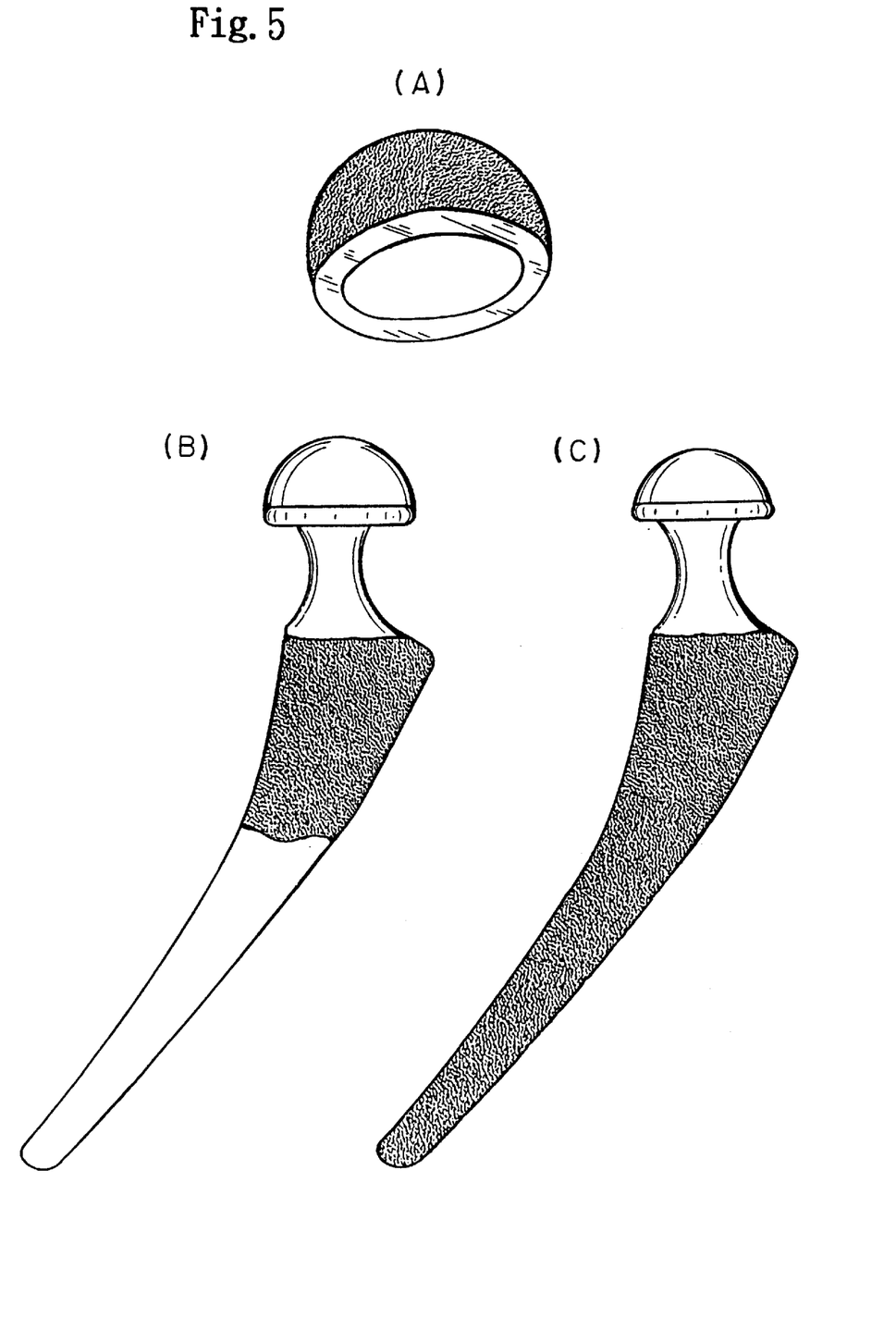

Titanium or titanium alloy (for example, Ti-6Al-4V) is formed into a continuous network of foam metal sheet, having an open-cell size of 0.5 mm~1.5 mm. Preferably an average size of the open-cell is 1.0 mm which is close to open size of the cancellous bone structure. The thickness of the sheet will be from 1.5 mm to about 3 mm, depending on the open-cell size, so that at least three (3) layers of the open-cell structure will be included within the foam-shaped network sheet. FIG. 5(A) shows an example of a case when the entire outer spherical surface of the cup is covered with the foam-shaped network sheet. However, the application of said sheet is not limited to this manner, the sheet can also be applied to cover a portion of the cup. If the thickness is less than 1.5 mm, many unconnected cell skeletons are revealed in the sheet, causing the mechanical weakness. On the other hand, if the thickness of the sheet exceeds 3 mm, there are two choices, one is the reduction of thickness of metallic acetabular cup or the other alternative is increasing the amount of bone to be removed to accommodate the thickened acetabular cup portion. Either one of these choices is not preferred.

The same argument can be applied to the femoral prothesis. Although it is not necessary to cover the whole stem portion (that is from the proximal portion right under the collar part of the stem to the distal end portion) with the Ti or T-based alloy foam-shaped network sheet, said foam sheet can be adhered to only the proximal portion (see FIG. 5(B)), or the entire stem portion (see FIG. 5(C)).

The network sheet which is cut in an appropriate dimension is bonded to the solid metallic substrates of the acetabular cup and femoral stem. The bonding can be achieved by the solid state or liquid-phase involved joining techniques. The latter technique may include the laser welding, soldering or fusion welding. However, it is preferable to utilize the solid-state diffusion bonding, since titanium is one of the typical materials which can be jointed successfully by the solid-state diffusion bonding technique.

Alternatively, the casting technique can be used to fabricate to cup and stem with entirely or partially covered with the foam-shaped network using a cast-in-cast method or the lost wax technique.

Electroplating method can also be applied to produce foamed titanium sheet. Untreated reticulated urethane foam substrate can be electroless-plated.

Accordingly, the solid prostheses of an acetabular cup and a femoral stem are covered entirely or partially with the titanium or titanium-based alloy foam-shaped network sheet with an average open-cell size of 1 mm and an average e thickness ranging from 1.5 mm to 3 mm. The open-cells of said network are then impregnated with the reinforced bone cement which is described in the following.

In our experiments, selected oxides are mixed with polymethyl methacrylate powder with a certain volume per cent and polymerized into a stainless steel mold (25×2×2 mm). After curing, the sample was subjected to a transverse rupture strength and modulus of elasticity measurements under a cross head speed of 1 mm/cm. For each group, five samples were prepared. The results are averaged out for five individual data points.

The following tables show the results.

TABLE 1

Effect of aluminum oxide addition
( ): standard deviation

| sample | break strength (MPa) | modulus of elasticity (GPa) |
| --- | --- | --- |
| PMMA (control) | 58.23 (1.54) | 1.5 (0.14) |
| $Al_2O_3$ 5 vol. % | 58.39 (1.22) | 1.6 (0.23) |
| 10 vol. % | 60.79 (2.10) | 1.9 (0.33) |
| 15 vol. % | 63.76 (1.92) | 1.8 (0.31) |
| 20 vol. % | 59.15 (2.08) | 1.5 (0.21) |
| 25 vol. % | 50.43 (1.87) | 1.5 (0.23) |
| 30 vol. % | 50.37 (1.22) | 1.3 (0.17) |

By admixing aluminum oxide particles to polymethyl methacrylate resin did not show a significant improvement in terms of mechanical properties, as seen in this table, although a slight increasing the mechanical properties is noticed when 5~20 vol. % of alumina was added.

TABLE 2

Effect of titanium oxide addition
( ): standard deviation

| sample | break strength (MPa) | modulus of elasticity (GPa) |
|---|---|---|
| PMMA (control) | 58.23 (1.54) | 1.5 (0.14) |
| TiO$_2$ 5 vol. % | 54.75 (0.98) | 1.4 (0.12) |
| 10 vol. % | 48.71 (1.43) | 1.4 (0.22) |
| 15 vol. % | 43.73 (1.54) | 1.5 (0.27) |
| 20 vol. % | 42.77 (1.96) | 1.3 (0.19) |
| 25 vol. % | 40.56 (1.57) | 1.3 (0.14) |
| 30 vol. % | 40.33 (1.52) | 1.2 (0.13) |

The similar conclusions as for the aluminum oxide addition can be found for titania addition. Again a slight improvement can be observed when 5 to 20 vol. % of titanium oxide particles are admixed.

TABLE 3

Effect of calcium oxide addition
( ): standard deviation

| sample | break strength (MPa) | modulus of elasticity (GPa) |
|---|---|---|
| PMMA (control) | 58.23 (1.54) | 1.5 (0.14) |
| CaO 5 vol. % | 48.42 (1.34) | 1.4 (0.16) |
| 10 vol. % | 39.99 (1.29) | 1.3 (0.15) |
| 15 vol. % | 35.38 (1.28) | 1.3 (0.23) |
| 20 vol. % | 33.24 (2.01) | 1.2 (0.21) |
| 25 vol. % | 30.56 (1.38) | 1.3 (0.15) |
| 30 vol. % | 30.11 (1.71) | 1.2 (0.12) |

There is no indication of improvements in mechanical properties when the calcium oxide particles are mixed to polymethyl methacrylate resin powders.

TABLE 4

Effect of hydroxyapatite addition
( ): standard deviation

| sample | break strength (MPa) | modulus of elasticity (GPa) |
|---|---|---|
| PMMA (control) | 58.23 (1.54) | 1.5 (0.14) |
| HA 5 vol. % | 64.57 (2.11) | 0.96 (0.12) |
| 10 vol. % | 60.56 (1.87) | 0.89 (0.13) |
| 15 vol. % | 47.97 (1.55) | 0.87 (0.17) |
| 20 vol. % | 48.09 (1.15) | 0.79 (0.14) |
| 25 vol. % | 49.29 (1.76) | 0.78 (0.21) |
| 30 vol. % | 50.21 (1.44) | 0.72 (0.17) |

Within a limited addition ranging from 5 to 10 vol. % of synthetic hydroxyapatite, a slight increasing in break strengths was noted. However, surprisingly no improvements in modulus of elasticity was indicated in all ranges of additive per cent.

TABLE 5

Effect of magnesium oxide addition
( ): standard deviation

| sample | break strength (MPa) | modulus of elasticity (GPa) |
|---|---|---|
| PMMA (control) | 58.23 (1.54) | 1.5 (0.14) |
| MgO 5 vol. % | 65.79 (1.45) | 1.9 (0.23) |
| 10 vol. % | 70.34 (1.33) | 2.1 (0.33) |
| 15 vol. % | 72.45 (1.90) | 2.2 (0.20) |
| 20 vol. % | 71.66 (1.33) | 2.0 (0.32) |
| 25 vol. % | 67.43 (1.21) | 1.8 (0.09) |
| 30 vol. % | 65.46 (1.82) | 1.7 (0.13) |

For all ranges of volume % addition of magnesium oxide particles, both break strength and modulus of elasticity were significantly improved. More specifically, the said improvement can be more intensified in a range of 10 to 15 vol. %.

TABLE 6

Effect of zirconium oxide addition
( ): standard deviation

| sample | break strength (MPa) | modulus of elasticity (GPa) |
|---|---|---|
| PMMA (control) | 58.23 (1.54) | 1.5 (0.14) |
| ZrO$_2$ 5 vol. % | 59.75 (1.92) | 2.6 (0.11) |
| 10 vol. % | 62.35 (1.60) | 2.7 (0.30) |
| 15 vol. % | 64.40 (1.19) | 2.6 (0.47) |
| 20 vol. % | 62.21 (1.51) | 2.4 (0.24) |
| 25 vol. % | 57.36 (1.70) | 2.1 (0.22) |
| 30 vol. % | 56.77 (2.09) | 2.2 (0.31) |

Similar findings can be applied to the case when zirconium oxide particles are added, specifically the additive effect appears significant in a range of 10 to 20 vol. %.

In the above, alumina, magnesia, and zirconia exhibit beneficial effects on improving mechanical properties. Hence, in addition to applying aluminum foam-shaped network sheet, these metallic oxides are also admixed. In the following table, MP II indicates the metal primer II (a product from G corporation).

TABLE 7

Effect of inserting aluminum network sheet
and several oxide particles addition
( ): standard deviation

| sample | break strength (MPa) | modulus of elasticity (GPa) |
|---|---|---|
| PMMA (control) | 58.23 (1.54) | 1.5 (0.14) |
| Al network | 69.61 (2.01) | 2.7 (0.12) |
| Al network + MP II | 72.74 (3.02) | 3.2 (0.33) |
| Al network + Al$_2$O$_3$ 5 vol. % | 73.75 (2.90) | 2.8 (0.19) |
| 10 vol. % | 75.95 (3.11) | 3.1 (0.24) |
| 15 vol. % | 74.35 (1.99) | 3.0 (0.18) |
| Al network + MP II + Al$_2$O$_3$ 15 vol. % | 80.45 (2.18) | 3.3 (0.67) |
| Al network + MP II + MgO 15 vol. % | 85.20 (2.29) | 3.7 (0.11) |
| Al network + MP II + ZrO$_2$ 15 vol. % | 79.37 (1.94) | 3.9 (0.34) |

Several important conclusions can be drawn from these data;
1) By impregnating metallic (in this study, aluminum foam metal is used) network sheet by un-reinforced polymethyl methacrylate, 20% improvement in strength and 80% improvement in MOE were noticed.
2) Furthermore, if MP II droplet is applied when metallic sheet is impregnated by the PMMA, 30% of strength and 100% (in other words, doubled) of MOE were improved.
3) Moreover, if a certain amount of oxide (for example, alumina) is admixed with polymeric resin powder (PMMA) prior to impregnating the metallic network sheet, about same extent of improvements as the previous case can be found.
4) As indicated in last three columns in Table 7, if 15 vol. % of alumina, magnesia, or zirconia was admixed to the polymer powder along with a droplet of MP II prior to impregnate the aluminum network sheet, remarkable improvements in both strengths and MOE are noticed.
5) Since for the case of using Al foamed sheet, the MOE value was improved as much as about 2.7 times as compared to that of PMMA control, hence it can be expected that if Ti foamed sheet is used, the resultant improved MOE value will be more than 10 GPa which is higher than those of the bone structure.

Although metal oxides is individually admixed to the polymer powders in the above tests, a combination of alumina, magnesia, and zirconia can further improve the mechanical properties.

Regarding the physical properties, several selected samples are subjected to measurements of temperature rise during the polymerization and a linear polymerization shrinkage. The selected samples are; (1) untreated PMMA, serving as a control sample, (2) 15 vol. % $Al_2O_3$ added PMMA (from Table 1), (3) 15 vol. % MgO added PMMA (from Table 5), (4) 15 vol. % $ZrO_2$ added PMMA (from Table 6), (5) Al network sheet impregnated by un-reinforced PMMA (from Table 7), (6) Al network sheet+MP II+15 vol. % alumina added PMMA (from Table 7), (7) Al network sheet+MP II+15 vol. % magnesia added PMMA (from Table 7), and (8) Al network sheet+MP II+15 vol. % zirconia added PMMA (from Table 7). The obtained results are shown in Table 8.

TABLE 8

Temperature rise and polymerization shrinkage
( ): standard deviation

| sample No. | temperature rise (° C.) | polymerization shrinkage (%) |
| --- | --- | --- |
| 1 | 74.4 (0.4) | 2.3 (0.09) |
| 2 | 65.4 (0.4) | 1.5 (0.09) |
| 3 | 58.3 (0.2) | 1.3 (0.11) |
| 4 | 50.2 (0.4) | 1.5 (0.10) |
| 5 | 49.3 (0.2) | 1.3 (0.11) |
| 6 | 48.9 (0.3) | 1.3 (0.13) |
| 7 | 47.9 (0.2) | 1.3 (0.11) |
| 8 | 45.9 (0.3) | 1.1 (0.08) |

From Table 8, it was found that (1) zirconia is a very effective oxide to suppress the temperature rise and polymerization shrinkage, if the oxide alone is added to PMMA powder resin, (2) aluminum network sheet exhibits another effective function to improve the above mentioned physical properties, and (3) furthermore, a combination of the aluminum network sheet, zirconia, and metal primer provides the best result.

As a result, according to the present invention, an improved orthopedic implant system possesses biological, mechanical and morphological compatibilities. All materials used for said systems is biologically safe and compatible to receiving vital hard and soft tissues. With respect to mechanical compatibility, as discussed previously in details, the foam metal network being impregnated with reinforced bone cement (mainly consisted of polymethyl methacrylate resin and metallic oxides) exhibits the intermediate values in mechanical strength and modulus of elasticity between those for the solid CPT or Ti-based alloys cup and stem and those for reinforced PMMA bone cement. Hence, even under the discontinuous stress field, the load can be smoothly transmitted and the mechanical compatibility can be achieved.

Finally, a continuously connected ligamented, reticulated open-cell geometry of the foam metal network having a duodecahedronal cell shape is morphologically compatible to receiving bone, particularly the cancellous (or spongy) bone structure.

Embodiment

A production trial was carried out to fabricate a titanium foam metal sheet. For the present trial, a commercially available aluminum foam block which has an average open-cell size of about 1 mm diameter was employed. This block is a product from ERG, Inc., as described previously. A basic idea was to replicate the aluminum foam structure to be replaced by titanium metal. A molding cement was prepared and fed into open cells of the aluminum foam structure. After hardening the molding cement, the mold was heated in a furnace at 670° C. for about 1 hour to let all aluminum melt and flow out the mold. Then the mold with open-cells was placed into a vacuum-controlled casting machine for titanium. After the all titanium was solidified, the mold was removed from the casting machine and the molding cement was removed by using the air-borne particle blasting machine with fine particle of aluminum oxide. The surface topology of titanium foam sheet was observed to be identical to original aluminum open-cells.

Medical Applications

The presently invented orthotopic implant system can be applied as a total hip replacement and also applied to knee, elbow, shoulder, ankle, or finger(s). The reinforced PMMA can be used not only for a bone cement to form a cement mantle, but also can be employed solely to fabricate provisional crowns and bridges in dentistry.

While this invention has been described in details with respect to preferred embodiment and examples, it should be understood that the invention is not limited to that precise embodiments; rather many modifications, and variations would present themselves to those of skill in the art without departing from the scope and spirit of this invention, as defined in the appended claims.

What is claimed is:

1. An orthopedic implant system comprising an acetabular cup with an insert portion, a femoral stem with a ball head, and a reinforced bone cement comprising polymethyl methacrylate resin reinforced with metallic oxide particles, wherein at least a portion of an outer peripheral surface of said acetabular cup and at least a portion of an outer surface of said femoral stem are covered with a metallic foam-shaped network sheet which is at least partially impregnated with said reinforced bone cement.

2. The orthopedic implant system as claimed in claim 1, wherein said metallic foam-shaped network sheet is made of commercially pure titanium or a titanium-based alloy.

3. The orthopedic implant system as claimed in claim 1 or 2, wherein an average open-cell size of the metallic foam-shaped network is 1 mm, and an average thickness of said metallic foam-shaped network sheet is 3 mm.

4. The orthopedic implant system as claimed in claim 1 or 2, wherein said metallic foam-shaped network sheet is partially or entirely bonded onto said acetabular cup and said femoral stem through diffusion bonding.

5. The orthopedic implant system as claimed in claim 1 wherein said metallic oxide particles are selected from the group consisting of aluminum oxide, magnesium oxide, zirconium oxide, and mixtures thereof.

6. The orthopedic implant system as claimed in claim 1, wherein said metallic foam-shaped network sheet has a reticulated open cell geometry of duodecahedronal cell shapes.

* * * * *

UNITED STATES PATENT AND TRADEMARK OFFICE
CERTIFICATE OF CORRECTION

PATENT NO.    : 6,312,473 B1
DATED         : November 6, 2001
INVENTOR(S)   : Yoshiki Oshida It is certified that error appears in the above-identified patent and that said Letters Patent is hereby corrected as shown below:

Title page,
Item [57], ABSTRACT, line 4, should read as follows:
"Solid metal femoral stem (entirely or partially) and solid metal acetabular head (entirely or partially) are";

Column 1,
Line 29, "t he" should read -- the --;

Column 3,
Line 28, "comnatibility" should read -- compatibility --;

Column 6,
Line 67, "Formica" should read -- fluormica --;

Column 8,
Line 28, "to" should read -- the --;
Line 37, after "average" delete "e".

Signed and Sealed this

Ninth Day of April, 2002

Attest:

*Attesting Officer*

JAMES E. ROGAN
*Director of the United States Patent and Trademark Office*